(12) United States Patent
Toh

(10) Patent No.: US 6,257,722 B1
(45) Date of Patent: Jul. 10, 2001

(54) OPHTHALMIC APPARATUS

(75) Inventor: Minoru Toh, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/583,762

(22) Filed: May 31, 2000

(30) Foreign Application Priority Data

May 31, 1999 (JP) ................................................ 11-151425

(51) Int. Cl.$^7$ ....................................................... A61B 3/14
(52) U.S. Cl. ............................................................ 351/208
(58) Field of Search .................................... 351/204, 206, 351/208, 209, 210, 211, 221; 606/4, 5

(56) References Cited

U.S. PATENT DOCUMENTS

| | | |
|---|---|---|
| 5,507,799 | 4/1996 | Sumiya . |
| 5,562,656 | 10/1996 | Sumiya . |
| 5,562,691 | 10/1996 | Tano et al. . |
| 5,637,109 | 6/1997 | Sumiya . |
| 6,022,108 * | 2/2000 | Yoshida et al. ........................ 351/208 |
| 6,082,860 * | 7/2000 | Takagi .................................. 351/208 |

FOREIGN PATENT DOCUMENTS

| | | |
|---|---|---|
| 0 765 648 A2 | 4/1997 | (EP) . |
| 5-22667 | 1/1993 | (JP) . |
| 10-145654 | 5/1998 | (JP) . |

* cited by examiner

*Primary Examiner*—George Manuel
(74) *Attorney, Agent, or Firm*—Finnegan, Henderson, Farabow, Garrett & Dunner, L.L.P.

(57) ABSTRACT

An ophthalmic apparatus comprises an ophthalmic device having an observation optical system for observing a patient's eye and treating or examining the patient's eye, a moving device for relatively moving the ophthalmic device relative to the patient's eye, a photographing optical system including a plurality of photoelectric photographing elements for photographing the patient's eye, image capturing device which captures image signals of different ranges from the plurality of photoelectric photographing elements to obtain supplemental image data, a detecting device which analyzes the obtained image data to detect a position of the patient's eye, and a control device which controls the moving device based on the results detected by the detecting device to move the ophthalmic device to a desired position relative to the patient's eye.

14 Claims, 7 Drawing Sheets

E PUPIL   IRIS   SCLERA

OPHTHALMIC APPARATUS

BACKGROUND OF THE INVENTION

1. Field of the Invention

The present invention relates to an ophthalmic apparatus, and more particularly to an alignment mechanism of the apparatus relative to a patient's eye.

2. Description of Related Art

Referring to the ophthalmic apparatus such as an ophthalmic laser surgery apparatus, a refractometer, a noncontact tonometer, a fundus camera or the like, after the patient's eye fixes a fixation target to fix a position of an eyeball, a desired part of the patient's eye is aligned with the apparatus (such as optical axis of the following optical system: a laser irradiating optical system, a measuring optical system, a photographing optical system or the like) to carry out surgery, measurement, photographing or the like of the patient's eye. Deviation between the patient's eye and the apparatus may occur due to movement of the patient's eye (the eyeball) after alignment. Every time when the deviation occurs, manually-operated alignment is inconvenient. For this reason, currently, a mainly used type of apparatus is the one detects positional relationship between the patient's eye and the apparatus to move the apparatus relative to the patient's eye to perform alignment.

As for the ophthalmic laser treatment apparatus, it is well known that a corneal surgery apparatus which irradiates a corneal surface with an excimer laser beam to ablate a lesion on the corneal surface or to change the corneal curvature to correct refractive errors. For instance, in this kind of the apparatus, movement of the patient's eyeball may occur while the laser irradiating. However, the examiner may not recognize this movement and keeps the laser irradiating, which results in ablating the cornea in a not-predetermined shape. For the prevention of this error, it is suggested to provide the ophthalmic apparatus with a function of moving an irradiating optical axis of the laser irradiating optical system to perform tracking of the patient's eye. In this kind of tracking mechanism, an anterior part of the eye is consistently photographed with a CCD photographing element while the laser irradiating. Then, in the case of detecting that the pupil center position or the like are not positioned within a predetermined allowable range relative to the irradiating optical axis or the like as a standard position, the tracking of the irradiating optical axis is performed in a manner to make the pupil center position or the like coincide with the standard position based on the photographing image.

As for the above-mentioned CCD photographing element for position detecting, a CCD photographing element for interlaced scanning which alternately outputs image data (image signals) of an odd field and of an even field is generally used because such a CCD photographing element is economical. However, this CCD photographing element requires about 33 ms to obtain a screenful of image data. For this reason, in case that the movement of the patient's eye is fast, it results in decreasing accuracy of tracking and operation.

In addition, it is suggested that the apparatus which projects target luminous flux on the patient's cornea and photographs a target image (bright spot) formed on the cornea with the CCD photographing element to perform tracking based on the results. However, in case that the patient's eye moves fast, which results in decreasing accuracy of tracking and surgery.

SUMMARY OF THE INVENTION

The present invention has been made in view of the above circumstances and has an object to overcome the above problem and to provide the ophthalmic apparatus which can increase accuracy of surgery or measurement by speeding up alignment of the patient's eye and the apparatus.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed our in the appended claims.

To achieve the objects and in accordance with the purpose of the invention, as embodied and broadly described herein, an ophthalmic apparatus comprises ophthalmic means having an observation optical system for observing a patient's eye and treating or examining the patient's eye, moving means for relatively moving the ophthalmic means relative to the patient's eye, a photographing optical system including a plurality of photoelectric photographing elements for photographing the patient's eye, image capturing means which captures image signals of different ranges from the plurality of photoelectric photographing elements to obtain supplemental image data, detecting means which analyzes the obtained image data to detect a position of the patient's eye, and control means which controls the moving means based on the results detected by the detecting means to move the ophthalmic means to a desired position relative to the patient's eye.

In another aspect of the present invention, an ophthalmic apparatus comprises ophthalmic means having an observation optical system for observing a patient's eye and treating or examining the patient's eye, moving means for relatively moving the ophthalmic means relative to the patient's eye, a photographing optical system including a plurality of photoelectric photographing elements for photographing the patient's eye, detecting means which captures images signals of interlaced scanning from the plurality of photoelectric photographing elements at time intervals and detects a position of the patient's eye based on the captured image signals, and control means which controls the moving means based on the results detected by the detecting means to move the ophthalmic means to a desired position relative to the patient's eye.

BRIEF DESCRIPTION OF THE DRAWINGS

The accompanying drawings, which are incorporated in and constitute a part of this specification illustrated and embodiment of the invention and, together with the description, serve to explain the objects, advantages and principles of the invention. In the drawings.

DETAILED DESCRIPTION OF THE PREFERRED EMBODIMENTS

Embodiment 1

A detailed description of one preferred embodiment of an ophthalmic apparatus embodying the present invention will now be given referring to the accompanying drawings.
[General Configuration]

Figure 1:
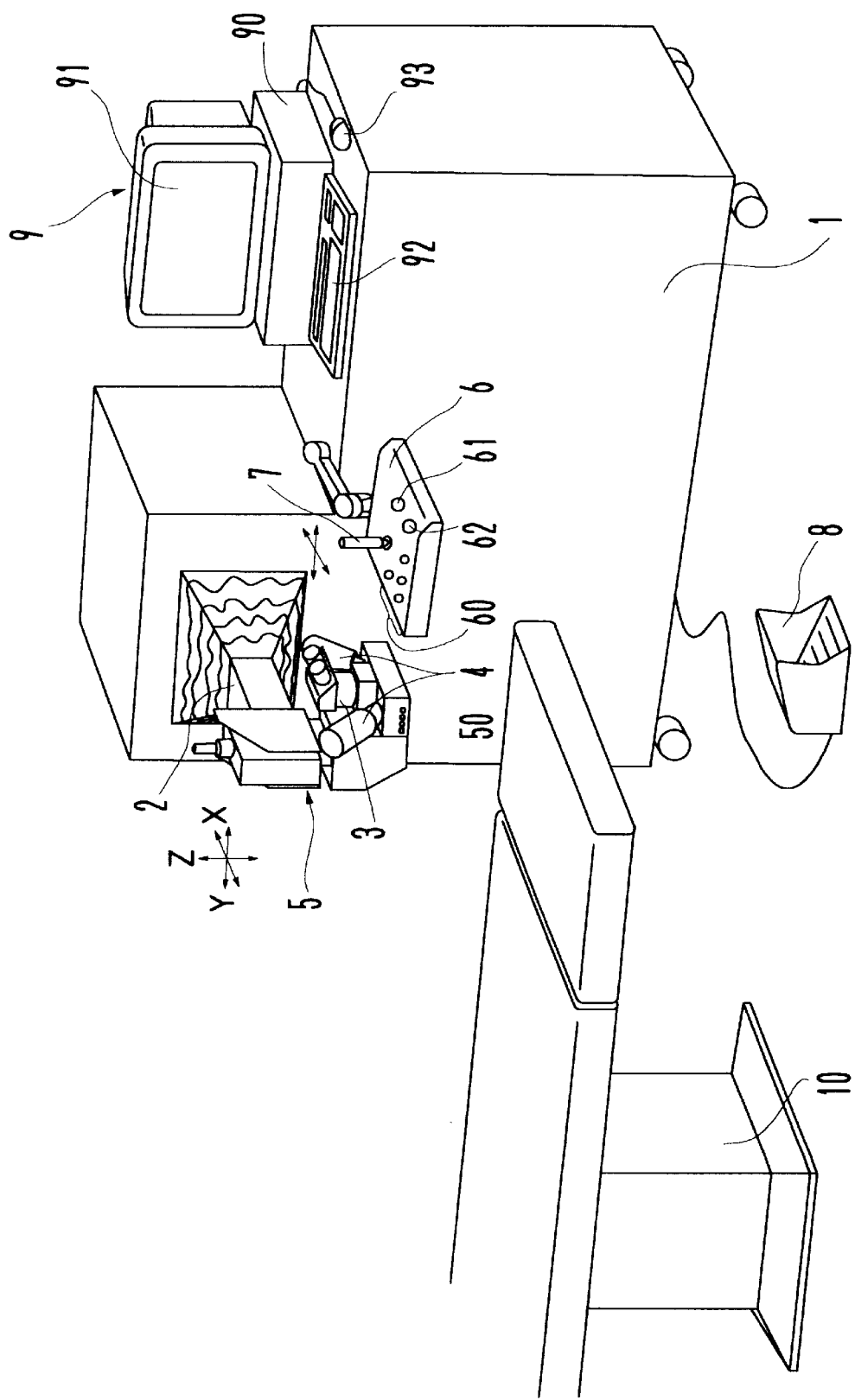
FIG. 1 is a whole view showing a configuration of a corneal surgery apparatus of the preferred embodiment consistent with the present invention.
Figure 2:
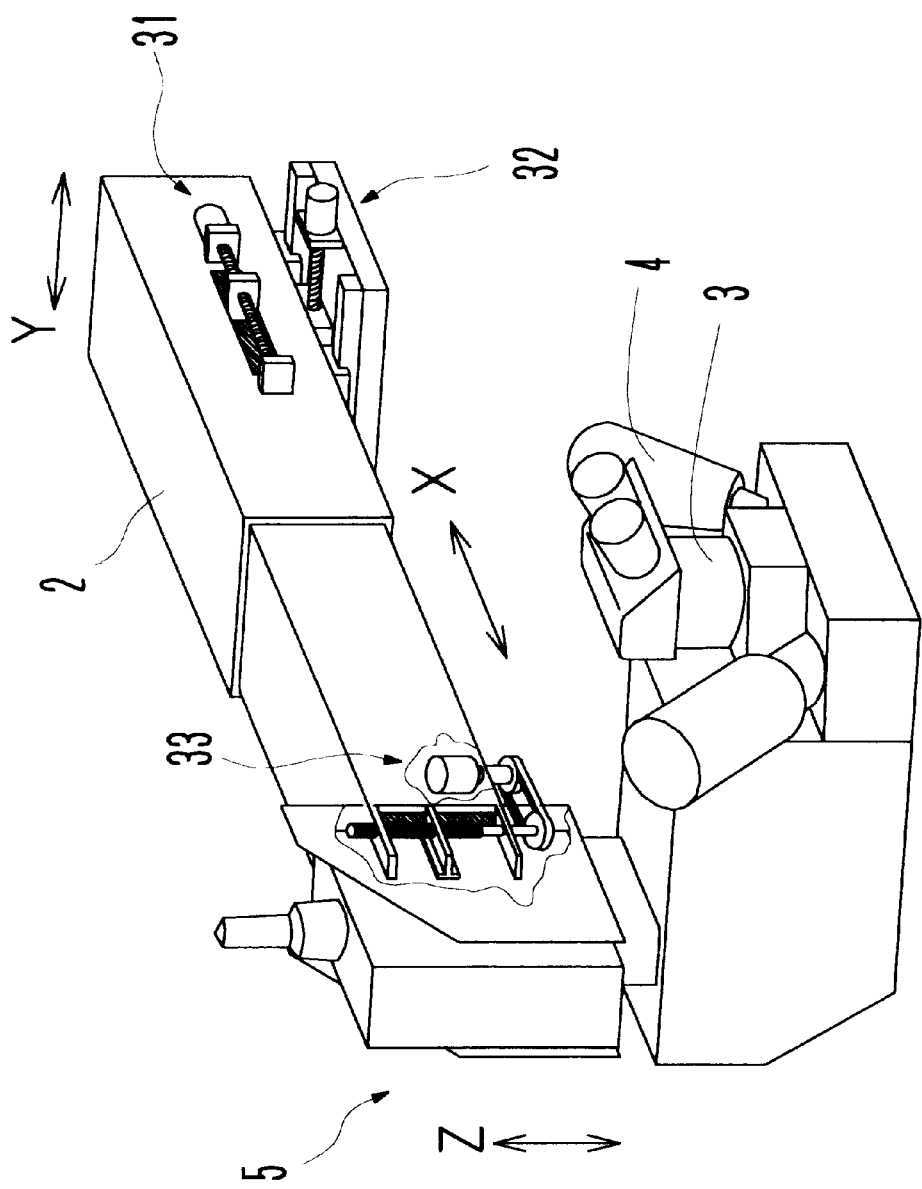
FIG. 2 is a view showing a moving mechanism of an arm unit and an arm tip unit in the corneal surgery apparatus.

FIG. 1 is a view showing a whole schematic configuration of a corneal surgery apparatus, which carries out corneal surgery with an excimer laser beam. Reference numeral 1 is a main body of the apparatus including an excimer laser light source and the like. Reference numeral 2 is an arm unit which guides the excimer laser beam emitted from the main body 1 to an arm tip unit 5 provided with a laser beam irradiating exit. The arm tip unit 5 further is provided an observation optical system including a binocular microscope unit 3 and an illuminating unit 4, and an eyeball position detecting optical system and the like, which will be described later in details. The arm unit 2 is moved in a X direction (a right-and-left direction relative to an examinee) with a X-direction arm driving device and in a Y direction (a back-and-forth direction relative to an examinee) with a Y-direction arm driving device 32. Additionally, the arm tip unit 5 is moved in a Z direction (a direction of an irradiating optical axis) with a Z-direction arm driving device 33. Each of the arm driving devices is provided with well-known configurations such as a motor or a sliding mechanism (See FIG. 2).

Reference numeral 6 is a controller provided with a joystick 7, which gives signals to drive the arm unit 2 in X and Y directions and various operation switches and the like. Various signals from the controller 6 are sent to a arithmetic control unit 30 mentioned later. Reference numeral 8 is a foot switch, which sends a trigger signal directing laser beam emission to the arithmetic control unit 30. Reference numeral 9 is a computer including a main body 90, a monitor 91, a keyboard 92, a mouse 93 and the like carries out the input of various data regarding required surgery condition, calculation of laser beam irradiation data, display, memorization and the like. Reference numeral 10 is a bed for the patient lying.
[Configuration of Each Unit]

Figure 3:
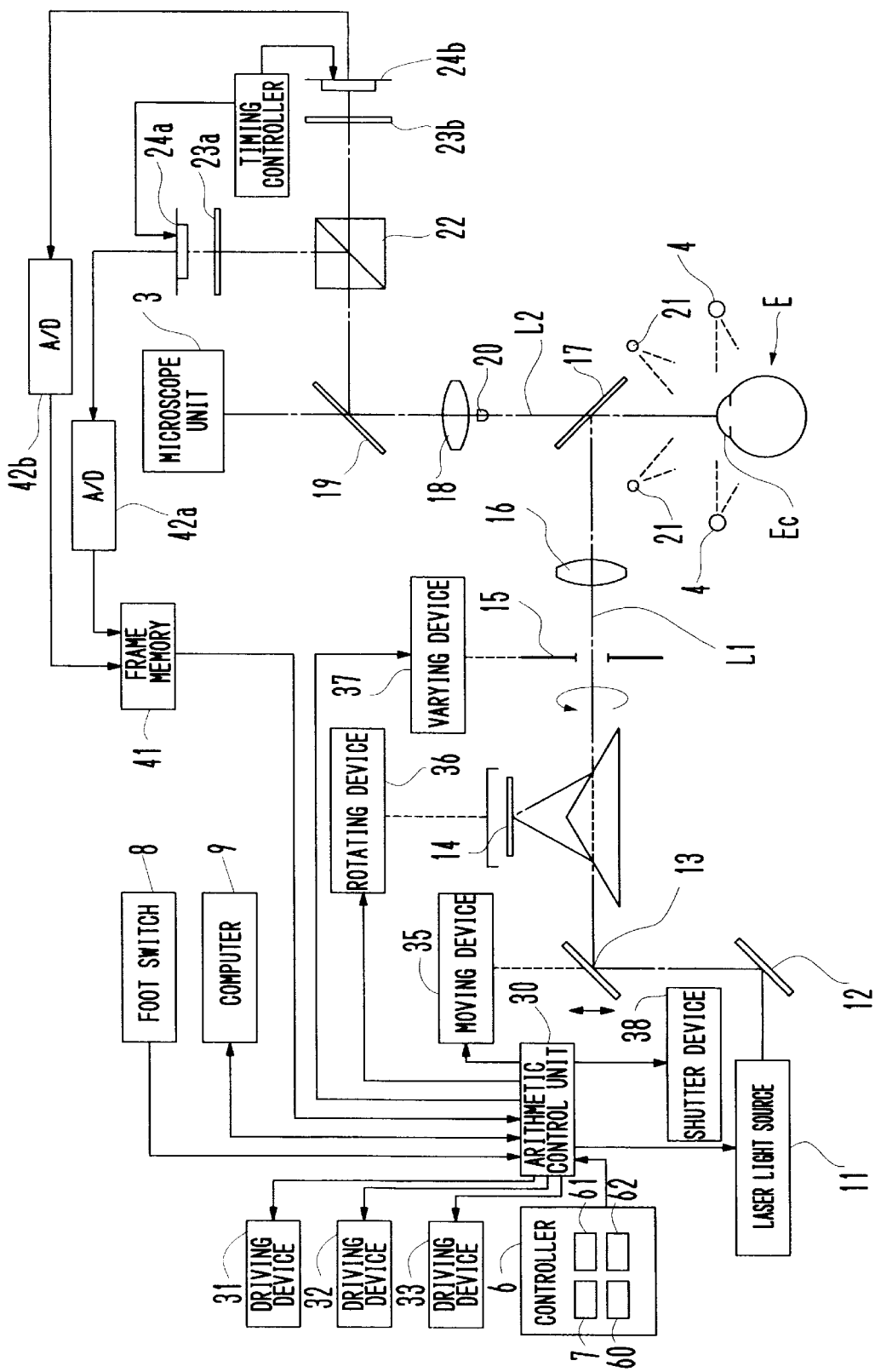
FIG. 3 is a schematic view showing a configuration of an optical and a control systems in the corneal surgery apparatus.

FIG. 3 is a schematic view showing a configuration of an optical and a control systems in the present apparatus.

Laser Beam Irradiating Optical System

Reference numeral 11 is a light source emitting the excimer laser beam of wavelength 193 nm (hereinafter, also referred to simply as a laser beam). The laser beam having a rectangular cross section emitted from the laser light source 11 is reflected with plane mirrors 12 and 13. The mirror 13 is moved in parallel to itself by a moving device 35 so as to move the laser beam in a fixed direction in a manner to cover the whole region of an aperture 15. Reference numeral 14 is an image rotator, which is rotated by a rotating device 36 to rotate the laser beam reflected by the mirror 13 about an irradiating optical axis L1. Reference numeral 15 is the aperture for restricting the irradiation range of the laser beam and varied the aperture diameter by a varying device 37. Reference numeral 16 is a projecting lens which projects the aperture 15 on the cornea Ec of the patient's eye E. The aperture 15 is in a conjugate position with the cornea Ec through the projecting lens 16. The range restricted by the aperture 15 is projected to the cornea Ec to determine an ablation range. For the detailed description, U.S. Pat. No. 5,507,799(corresponding to JP unexamined publication HEI 4(1992)-242644), U.S. Pat. No. 5,637,109 (corresponding to JP unexamined publication HEI 6(1994)-114083) and the like, which disclose in this kind of an optical system.

Reference numeral 17 is a dichroic mirror which is characteristically reflects the excimer laser beam and transmits visible light and infrared light, and makes the irradiating optical axis L1 of a laser irradiating optical system coaxial with and a detecting optical axis L2 of the observation optical system and of the eyeball position detecting optical system described later.

Observation Optical System

Reference numeral 18 is an objective lens. Reference numeral 19 is a dichroic mirror which is characteristically transmits visible light and reflects infrared light. Luminous flux of an image of the anterior part of the eye E illuminated by visible illuminating light from the illuminating unit 4 is made incident to the microscope unit 3 through the dichroic mirror 17, the objective lens 18 and the dichroic mirror 19. This allows an examiner to observe the eye E with the binocular microscope unit 3. An unillustrated reticle plate is inserted in the observation optical system so that it can be set a standard of alignment in X and Y directions relative to the eye E.

Additionally, a target projecting optical system including two slits for alignment of a Z direction is disposed in the observation optical system (See U.S. Pat. No. 5,562,656 corresponding to JP unexamined publication HEI 6(1994)-47001). Reference numeral 20 is a fixation light disposed on the detecting optical axis L2.

Eyeball Position Detecting Optical System

Reference numeral 21 is an infrared illumination light sources 21 such as LED. Four infrared illumination light sources are disposed at 90° intervals about the illuminating optical axis L1 (the detecting optical axis L2). Reference numeral 22 is a beam splitter. Reference numerals 23a and 23b are infrared light transmitting filters. Reference numerals 24a and 24b are infrared CCD imagers. Each photographing surface of the infrared CCD imagers 24a and 24b is disposed in an approximately conjugate position with the vicinity of the pupil of the eye E relative to the objective lens 18 so that each position of pixels of the CCD imagers 24a and 24b coincides each other relative to the detecting optical axis L2 separated by the beam splitter 22. The luminous flux of the image of the anterior part of the eye E illuminated by the infrared illumination light from the light sources 21 passes through the dichroic mirror 17 and the objective lens 18 and is reflected by the dichroic mirror 19. Then, it forms an image on each photographing surface of the CCD imagers 24a and 24b respectively through the beam splitter 22 and the infrared light transmitting filters 23a and 23b. At this moment, the infrared light transmitting filters 23a and 23b cut the visible light, which is slightly reflected by the dichroic mirror 19. The CCD imagers 24a and 24b respectively adopt an interlaced method.

Control System

Reference numeral 30 is the arithmetic control unit for driving and controlling the whole apparatus including the laser light source 11, the moving device 35, the rotating device 36, the varying device 37, a shutter device 38 described later, each of arm driving devices 31, 32, 33 and the like. The arithmetic control unit 30 is connected to a frame memory 41. Each of image data outputted by the CCD imagers 24a and 24b on the basis of synchronizing signals from a timing controller 40 is captured into the frame memory 41.

[Capturing Images]

Figure 4:
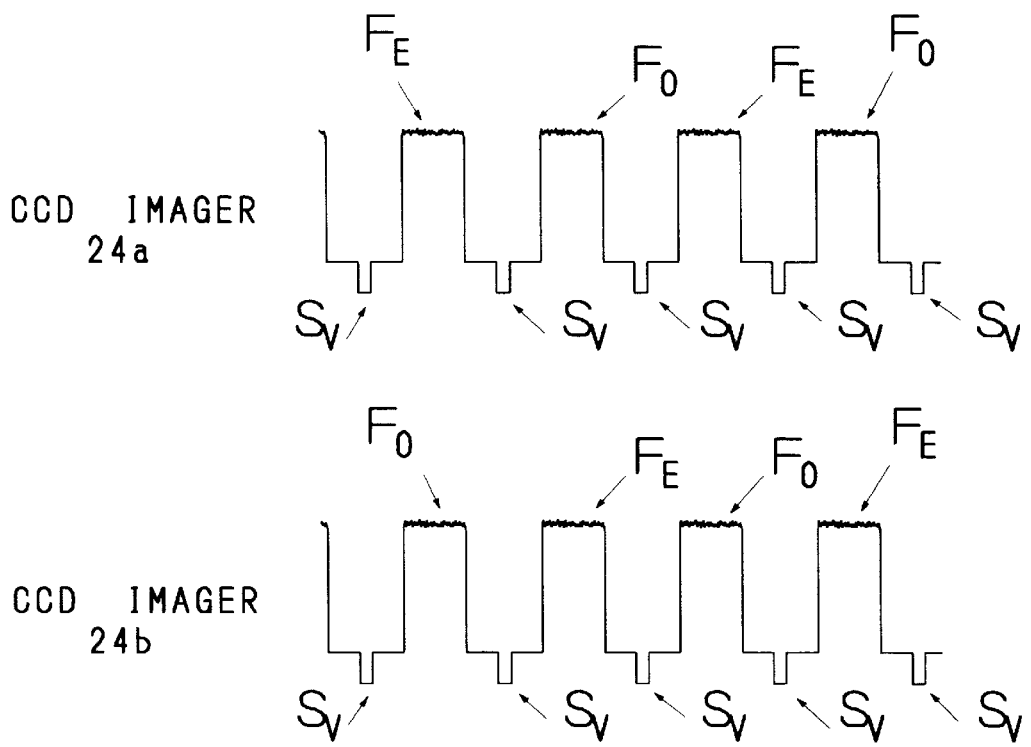
FIG. 4 is a view showing image signals outputted from the CCD imagers.

Capturing image into the frame memory 41 is explained referring to FIG. 4. FIG. 4 shows time-sequence change of each image signal outputted by the CCD imagers 24a and 24b.

A vertical-synchronizing signal VSYNC is transmitted from the timing controller 40 to the CCD imagers 24a and 24b at the same time. Every time when the vertical-synchronizing signal $V_{SYNC}$ from the timing controller 40 is inputted, the CCD imagers 24a and 24b output image data (image signals) of an odd field $F_O$ and image data of an even field $F_E$ (image signals) alternately at the same time. Here, when outputting the image data (image signals) of the even filed $F_E$ by the CCD imager 24a, the timing of both interlace scanning is alternated so as to output the image data (image signals) of the odd field $F_O$ by the CCD imager 24b (See FIG. 4). The frame memory 41 can obtain one frame of image (screen) data by simultaneously capturing outputted image data (image signals) of $F_O$ ($F_E$) from the CCD imager 24a and outputted image data (image signals) of FE ($F_O$) from the CCD imager 24b both of which is outputted in response to one vertical-synchronizing signal $V_{SYNC}$. This provides faster capture-processing, which is two times as fast as a conventional method, in which a frame of image (screen) data is stored image data of $F_O$ (image signals) and of $F_E$ (image signals) with one CCD imager (a frame of image (screen) data is captured taking about half time).

As mentioned above, the arithmetic control unit 30 successively carries out image-processing to a frame of image (screen) data captured into the frame memory 41 and detects an eyeball position based on level of light quantity signals of all pixels (or predetermined pixels).

[Eyeball Position Detecting]

Figure 5:
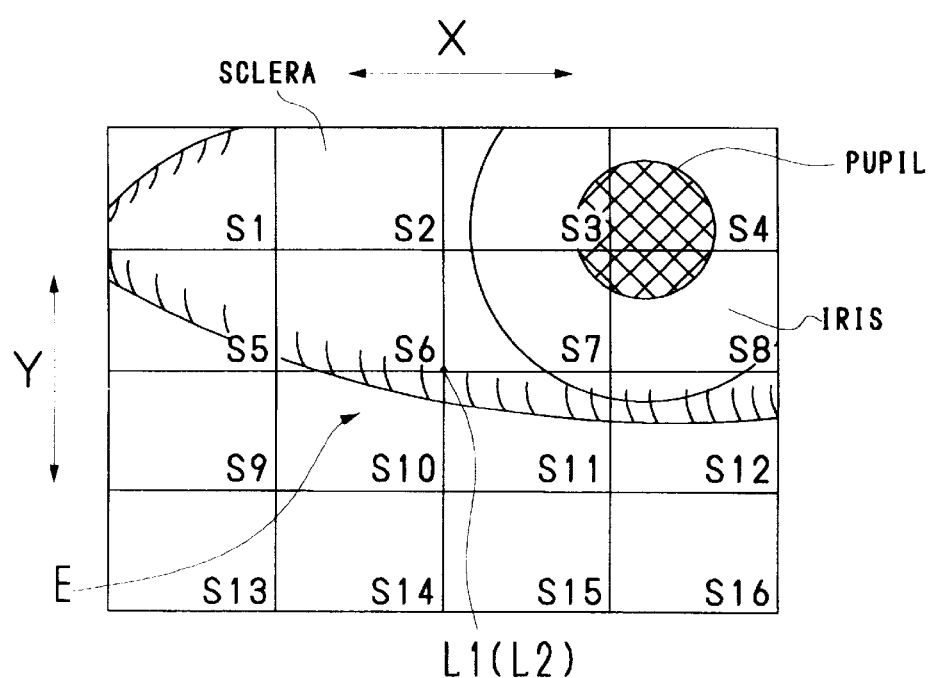
FIG. 5 is a view showing an example in which an image whose center is at the irradiating optical axis is divided into 16 areas.
Figure 6:
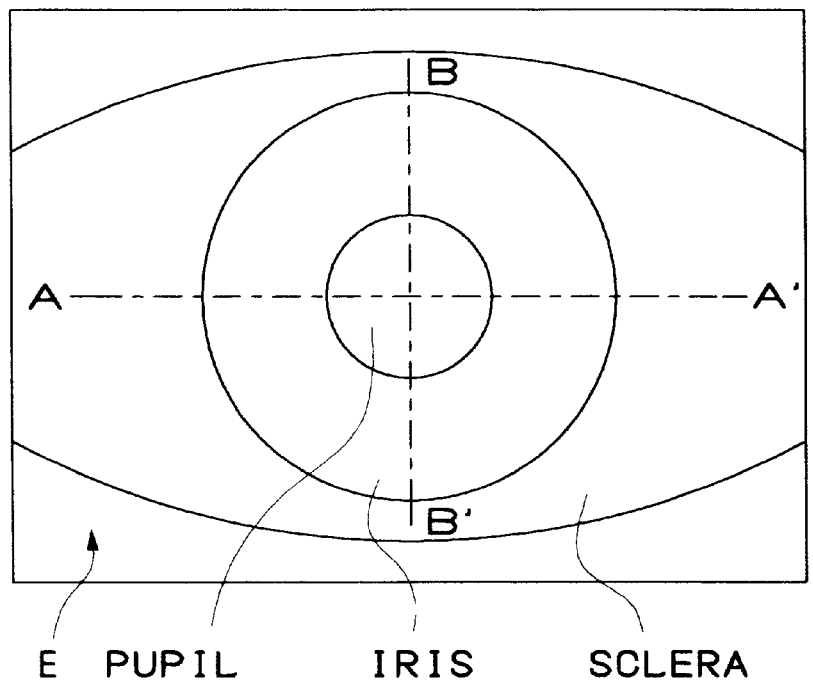
FIG. 6 is a view showing an image of an anterior part of the patient's eye photographed by the CCD imagers.
Figure 7:
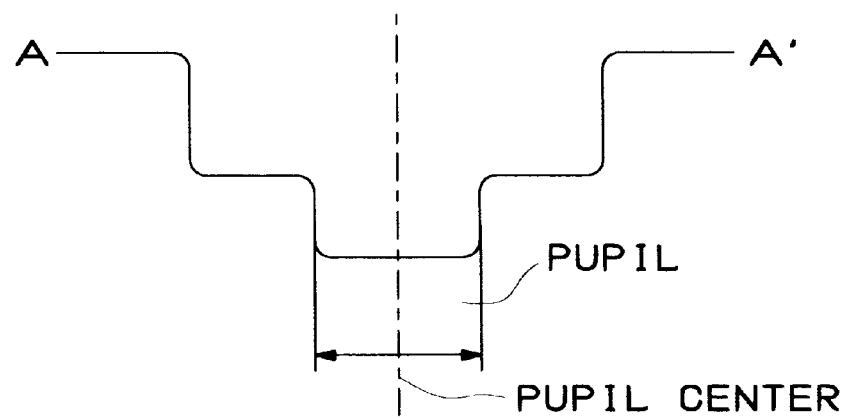
FIG. 7 is a view showing distribution of light quantity on the line A–A' in FIG. 6.

Next, a detecting method of the eyeball position is explained. In the present embodiment, detection of the pupil center position is explained, because the pupil center position is an object to be aligned with the irradiating optical axis L1. FIG. 5 is a view showing an example in which a photographing image (screen) whose center is at the irradiation optical axis L1 (the detecting optical axis L2) is divided into 16 areas. FIG. 6 is a view showing the image of the anterior part of the eye E photographed by the CCD imagers 24a and 24b. FIG. 7 is a view showing distribution of light quantity on the line A–A' in FIG. 6.

First, the light and dark information on the reflected light of the infrared light from the light sources 21 is detected. In this detection, as indicated in FIG. 5, the image whose center is at the irradiating optical axis L1 (the detecting optical axis L2), are divided into 16 areas (S1~S16) by dividing each side of the image into four in a two-dimensional image obtained by each of image data (image signals) from the CCD imagers 24a and 24b. Among pixels within each area (125 pixel×125 pixel), a predetermined number of pixels, which are objects to detect light and dark information (for example, 64 pixels) are preset in order to evenly distribute them within the areas (all pixels may be detected, however processing speed can be faster in case that the required number of pixels are detected). After digitization with A/D circuits 42a and 42b, each of image data (image signals) outputted from the CCD imagers 24a and 24b is captured into the frame memory 41, further conducted predetermined processing, and then inputted into the arithmetic control unit 30. The arithmetic control unit 30 obtains light and dark information on the preset pixels in each area from inputted signals. Since the degree of light and dark in each pixel is digitized, there are provided digitized numeral values ranging from 0 to 255 in 256 scales (0 is the darkest side and 255 is the lightest side representing the light and dark degree).

Next, the arithmetic control unit 30 picks up light and dark numerical value information within predetermined range (for example, 20 scales from the lowest light and dark numerical value) based on the lowest (darkest) scale of light and dark value on the basis of the light and dark value in the preset pixels in each area. The number of pixels, which has the light and dark numerical value within the predetermined range is counted to determine whether there are more than the predetermined number of pixels (for example, 20 pixels). In the event that there are the predetermined number of pixels (20 pixels) or more, it is judged that a pupil (or an iris surrounding the pupil) is within the area. On the other hand, in event that the number of pixels are less than the predetermined number (20 pixels), it is judged that the pupil is not yet detected the reasons that only a part of pupil is within the area or that a portion leading a low light and dark numerical value such as eyelashes is in the area.

In case that there are several areas including the predetermined number of pixels (20 pixels) and there are the areas that are not adjacent to each other, comparison is made between the area including the largest number of pixels and the not-adjacent area to determine whether there is a predetermined gap in the number of pixels (for example, 10 pixels) therebetween. This is for differentiation the pupil from an eyelash and the like even if the eyelash is far from the pupil. Even in that case, if there is a gap between the number of the counted pixels, it is judged that a pupil is in the area with the larger number of pixels. In case that there is not predetermined gap in the number of pixels (10 pixels), it is judged that the pupil is not detected. In case that there is the predetermined gap in the number of pixels (10 pixels), the pupil is pinpointed to be within the area which has the largest number of counted pixels. Then, whether the number of counted pixels are even is determined in the four areas, S6, S7, S10 and S11, whose center are at the irradiating optical axis L1 (the detecting optical axis L2). In the event that unevenness is observed in the number of the counted pixels, the irradiating optical axis L1 is moved in a direction, which resolves the unevenness, based on a position of the pinpoint area, which includes the pupil. This allows the pupil to move close to the irradiating optical axis L1 and the approximately whole pupil (a pupil range) to be detected.

Additionally, in the above-mentioned detection of the pupil based on the light and dark information, the two-dimensional images obtained by each of image data (image signals) from the CCD imagers 24a and 24b can be divided into four areas with the irradiating optical axis L1 (the detecting optical axis L2) as the center.

After the approximately whole pupil (the pupil range) can be detected, then, the pupil center position is detected. As indicated in FIGS. 6 and 7, light quantity of the eye is different depending on the pupil, the iris and the sclera. This distribution of light quantity information enables coordinates of the pupil edge position to be detected. The coordinates of the pupil edge position provide the center position of the coordinates, that is, coordinates of the pupil center position. As for the eyeball position detecting, see EP 0767648 corresponding to JP unexamined publication HEI 9(1997)-149914 and HEI 10(1998)-192333 and the like by the present applicant.

[Operation of Apparatus]

Hereinafter, operation of the apparatus having configurations as mentioned above will be described.

After turning on power and getting the system up and running, a menu appears on a monitor 91 of the computer 9. There are two operation-modes: PRK (photorefractive keratectomy) and PTK (phototherapeutic keratectomy) in corneal surgery with the excimer laser beam. In this case, PRK is selected from the menu. An examiner inputs various data such as a pre-examined refractive power value of the eye E or operation condition with the keyboard 92 of the computer 9. The main body 90 of the computer 9 calculates operation data such as the amount of corneal ablation and the like based on inputted data. The calculated data is transmitted to the arithmetic control unit 30 with operation of the keyboard 92 or the mouse 93.

After completing preparation for the input, the examiner makes the patient lie down on the bed 10. The arm tip unit 5 having the laser beam irradiating exit is positioned above the eye E. Each light source comes on. The eye E fixes on the fixation light 20.

Using the microscope unit 3, the examiner observes the anterior part of the eye E illuminated by the illuminating unit 4 and operates the joystick 7 to make alignment in X and Y directions in a manner to position the unillustrated reticle plate and the pupil in a predetermined relationship and to make alignment a Z direction by operating a focus adjustment switch 60. After signals are inputted from the joystick 7 and the focus adjustment switch 60 into the arithmetic control unit 30, it activates each of arm driving devices 31, 32 and 33 to respectively move the arm unit 2 and the arm tip unit 5 in X and Y directions and in a Z direction.

Additionally, when making alignment, turning on an auto-alignment switch 61 on the controller 6 activates auto-alignment mechanism. In case that the eye E is in a position where the pupil range or more preferably, the pupil center position can be detected in the eye ball position optical system, the arithmetic control unit 30 drives each of arm driving devices 31 and 32 to move the arm unit 2 in X and Y directions in a manner that the pupil center position coincides with the irradiating optical axis L1.

Further, in case that the laser irradiating is performed while keeping the pupil center coincides with the irradiating optical axis L1, if a Ready switch 61 on the controller 6 is turned on, an auto-tracking mechanism is activated. In this case, the predetermined position on the CCD imagers 24*a* and 24*b* (in case that the auto-alignment is performed, a position of the irradiating optical axis L1 (the detecting optical axis L2)) is memorized as a standard position. The irradiating optical axis L1 is carried out tracking in a manner to coincide the pupil center position with the standard position (the arm unit 2 is moved in X and Y directions).

The pupil center position obtained by processing each of image data (the image signals) from CCD imagers 24*a* and 24*b* is compared with the standard position whenever necessary. In case that the eye E moves in a manner that the pupil center position moves outside of a predetermined first allowable range relative to the standard position (for example, a radius of 0.005 mm from the standard position), the arithmetic control unit 30 generates a tracking signal based on compared information. Then, it drives each of the arm driving devices 31 and 32, thereby and moves the arm unit 2 in X and Y directions to position the pupil center position within the first allowable range of the standard position.

Furthermore, in case that the eye E moves in a manner that the pupil center position moves outside of a predetermined second allowable range relative to the standard position (such as within a radius of 1 mm from the standard position), the arithmetic control unit 30 activates the shutter device 38 to stop the laser irradiating, then positions the pupil center position at least within the second allowable range with manually-operated alignment. This permits the arithmetic control unit 30 to position the pupil center position within the first allowable range of the standard position with the auto-tracking mechanism.

After the pupil center position is positioned within the first allowable range of the standard position with the auto-tracking mechanism, the shutter device 38 is activated again to be ready for the laser irradiating. Then, the examiner operates the foot switch 8 to allow the arithmetic control unit 30 to start the laser irradiating again. The laser beam is irradiated to the eye E through the irradiating optical system. The cornea Ec is ablated on the basis of the calculated operation data.

In case that the auto-tracking is carried out without using the auto-alignment based on a position of the irradiating optical axis L1 determined by the manually-operated alignment with the joystick 7, the irradiating optical axis L1 is positioned in a target position of the eye E with the manually-operated alignment. After Completing alignment and turning on the Ready switch 62, the pupil center position of the eye E at this time is memorized as the standard position (That is, the standard position in this case is different from the irradiating optical axis L1). Thus, the auto-tracking can be performed the same as the case of the auto-tracking.

As described above, according to the present invention, a frame of image (screen) data can be obtained at the speed about two times as fast as the conventional method, in which a frame of the image (screen) data is obtained with one CCD imager, and quick reaction to movement of the patient (tracking) is achieved.

Moreover, without capturing the image data (the image signals) of the odd field $F_O$ and of the even filed $F_E$ into the frame memory 41, either the image data (the image signals) of the odd field $F_O$ or of the even filed $F_E$ alone can be only captured into the frame memory 41. For instance, only the image data (the image signals) of the odd field $F_O$ is captured into the frame memory 41 from the CCD imager 24*a* in response to the input of the vertical synchronizing signals $V_{SYNC}$. The arithmetic control unit 30 detects the pupil center position based on the image data (the image signals) of the odd filed $F_O$. In response to the input of next vertical synchronizing signals $V_{SYNC}$, only the image data (the image signals) of the odd filed $F_O$ from the CCD imager 24*b* is captured into the frame memory 41. The arithmetic control unit 30 detects and processes the pupil center position based on the image data (the image signals) of the odd filed $F_O$ in the same fashion as mentioned above. A frame of image (screen) of data processed like this becomes coarse due to the fact that only either the odd filed $F_O$ or the even filed $F_E$ is captured. However, the capturing speed in this case is also two times as fast as the conventional one, which achieves speeding up of tracking.

Figure 8:
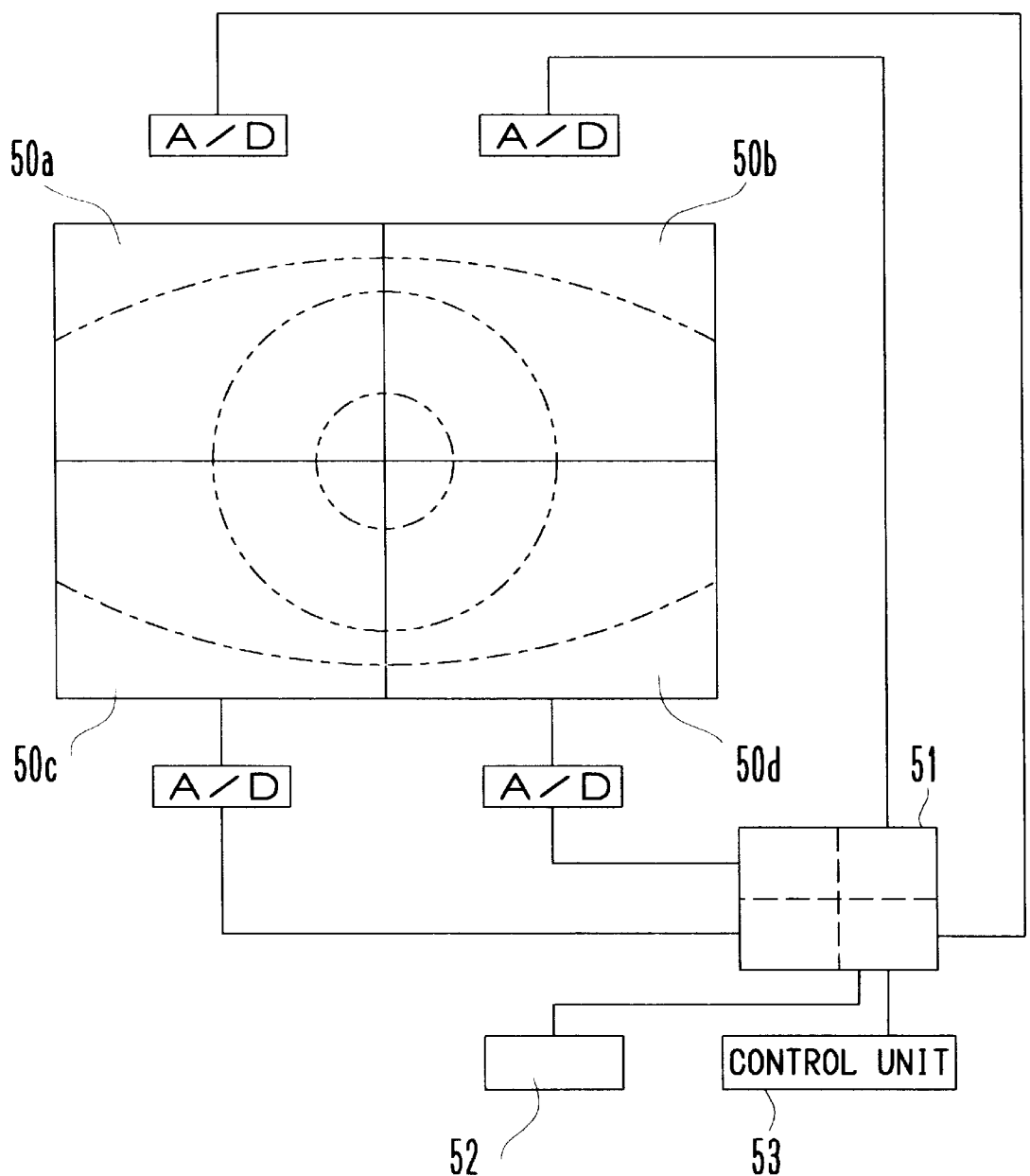
FIG. 8 is a view showing a modification of the CCD imagers.

Next, a modification of CCD imagers in the present invention is explained referring to FIG. 8 (explanation and illustration of unillustrated configurations in FIG. 8 is omitted since it is the same as the one mentioned before). In the above-mentioned eyeball position detecting optical system (FIG. 3), the beam splitter 22 divides the detecting (photographing) optical path. In the present modification, without using the beam splitter 22, the luminous flux of the image of the anterior part of the eye reflected by the dichroic mirror 19 is photographed with CCD imagers 50a, 50b, 50c and 50d by dividing the image into four ranges. Each of the CCD imagers 50a–50d are comprised of the quarter number of pixels compared with the case that the anterior part of the eye is photographed with one CCD imager. Accordingly, the scanning speed of a frame of the image data, which is outputted by each of CCD imagers 50a–50d, is four times as fast as the case that one CCD imager photographs the image of the anterior part of the eye E.

Each of the image data (the image signals) from the CCD imagers 50a–50d are simultaneously outputted based on the synchronizing signals from a timing controller 52 and captured into a frame memory 51. Capturing ranges of each of image data (the image signals) in the frame memory 51 correspond to disposition of each of CCD imagers 50a–50d. Thus, a frame of image (screen) data is comprised of each of the synthesized image data (the image signals). Thus, the frame memory 51 can capture the image (screen) data having the same number of pixels four times as fast as the conventional case that one CCD imager photographs the image of the anterior part of the eye E. The arithmetic control unit 53 detects and processes the pupil center position in the same fashion as the example mentioned before on the basis of the captured image data (screen) into the frame memory 51, and drives and controls each of the arm driving devices 31 and 32 based on the detected results.

The example in which the present invention is applied to a corneal surgery apparatus has been explained so far, yet the present invention is not limited by this example and can be carried out irrespective of configurations of the laser irradiating optical system. Additionally, the present invention can be applied to the optical apparatus for alignment or tracking relative to an eye to be examined such as the refractometer, the noncontact tonometer, the fundus camera or the like.

In the embodiment 1, the positional relationship between the patient's eye and the apparatus is detected on the basis of the pupil center position. The positional relationship may be also detected on the basis of the target image such as a Purkinje image with reflected luminous flux reflected by the patient's cornea.

Embodiment 2

The other preferred embodiment of the ophthalmic apparatus embodying the present invention will now be explained referring to the accompanying drawings.

Figure 9:
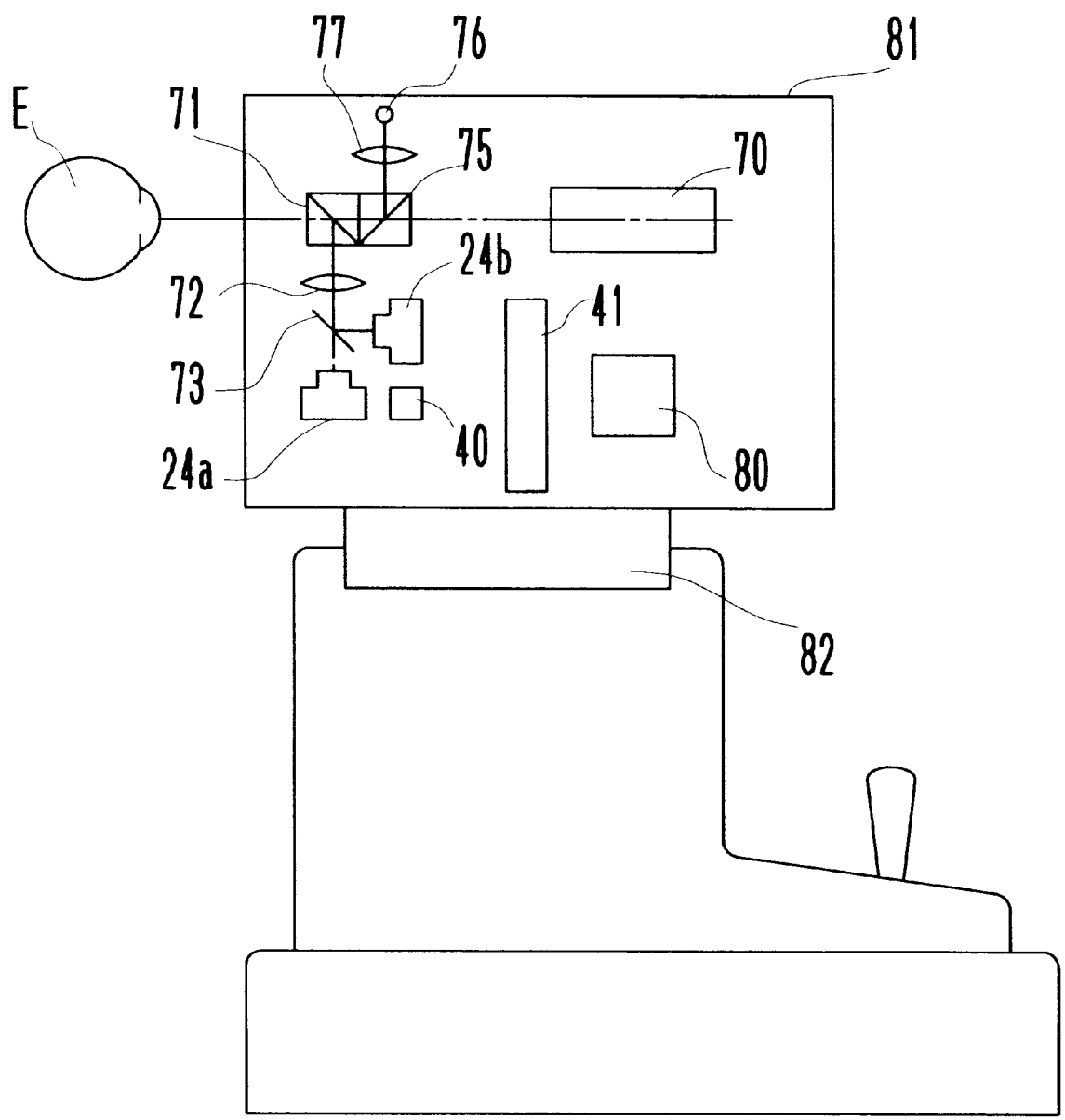
FIG. 9 is a schematic view showing a configuration of an optical and a control systems in an ophthalmic measuring apparatus of the preferred embodiment consistent with the present invention.

FIG. 9 is a view showing an example in which the present invention is applied to an ophthalmic apparatus having a measuring optical system 70 (for example, a refractive power measuring optical system), which measures the patient's eye E (the eye to be examined). In the drawings, components having the same configurations as the embodiment 1 have the same reference numerals.

In the eye E, a target image for alignment is formed with a light source 76, a lens 77, and beam splitters 75 and 71. The target image and the image of the anterior part of the eye E are formed on the two CCD imagers 24a and 24b by the beam splitter 71, the lens 72 and an optical path dividing mirror 73. As mentioned in the Embodiment 1, the frame memory 41 captures the image data (the image signals) $F_E$ ($F_O$) from the CCD imager 24a, and the image data (the image signals) of $F_O$ ($F_E$) from the CCD imager 24b synchronized and outputted by the synchronizing signal of the timing controller 40 are captured at the same time. A control unit 80 detects the target image based on a frame of the obtained image (screen) data to obtain a position of the measuring optical system 70 relative to the eye E. On the basis of the detected results, the control unit 80 drives and controls a driving mechanism 82, which moves a measuring unit 81 accommodated an optical system in a X direction (a right and left direction), a Y direction (an up and down direction) and a Z direction (a back and forth direction) to perform alignment and tracking thereof.

Needless to say, the modified configuration of the CCD imagers showing in FIG. 8 can be also applied in the case of the ophthalmic apparatus showing in FIG. 9.

Although the irradiating optical axis (measuring optical axis) L1 and the detecting optical axis L2 are made coaxially in the Embodiments 1 and 2, they do not necessary have to be coaxial as long as these axes are in a predetermined relative position. In this case, a position of the irradiating optical axis L1 relative to the detecting optical axis L2 must be stored beforehand.

As explained above, according to the present invention, while using economical photographing elements, the speed of alignment of the patient's eye and the apparatus can be increased, which results in high accuracy of the surgery or measurement.

The foregoing description of the preferred embodiment of the invention has been presented for purposes of illustration and description. It is not intended to be exhaustive or to limit the invention to precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto and their equivalents.

What is claimed is:

1. An ophthalmic apparatus comprising:
    ophthalmic means having an observation optical system for observing a patient's eye and treating or examining the patient's eye;
    moving means for relatively moving the ophthalmic means relative to the patient's eye;
    a photographing optical system including a plurality of photoelectric photographing elements for photographing the patient's eye;
    image capturing means which captures image signals of different ranges from the plurality of photoelectric photographing elements to obtain supplemental image data;
    detecting means which analyzes the obtained image data to detect a position of the patient's eye; and
    control means which controls the moving means based on the results detected by the detecting means to move the ophthalmic means to a desired position relative to the patient's eye.

2. The ophthalmic apparatus according to claim 1, wherein the plurality of photoelectric photographing elements include:
    one photoelectric photographing element disposed in a photographing optical path; and
    another photoelectric photographing element disposed in a divided optical path by a beam splitter disposed in the photographing optical path.

3. The ophthalmic apparatus according to claim 2, wherein the two photoelectric photographing elements are disposed such that each position of pixels of the photoelectric photographing elements coincides with each other relative to a principal optical axis of the photographing optical path in which each of the photoelectric photographing elements is disposed.

4. The ophthalmic apparatus according to claim 1, wherein the plurality of photoelectric photographing elements include one photoelectric photographing element disposed in a photographing optical path and another photoelectric photographing element disposed in a divided optical path by a beam splitter disposed in the photographing optical path; and the image capturing means obtains image data of an odd field from one of the photoelectric photographing elements and image data of an even field from another one of the photoelectric photographing elements approximately at the same time and those image data are combined to obtain a screenful of image data.

5. The ophthalmic apparatus according to claim 1, wherein the plurality of photoelectric photographing elements include four photoelectric photographing elements disposed about a principal optical axis of the photographing optical system.

6. The ophthalmic apparatus according to claim 1, wherein the detecting means includes means for obtaining a pupil edge of the patient's eye from the obtained image data.

7. The ophthalmic apparatus according to claim 1, wherein the detecting means includes means for obtaining a pupil center position of the patient's eye from the obtained image data.

8. The ophthalmic apparatus according to claim 1, wherein the ophthalmic means includes laser treatment means for treating the patient's eye with a treatment laser beam.

9. An ophthalmic apparatus comprising:

ophthalmic means having an observation optical system for observing a patient's eye and treating or examining the patient's eye;

moving means for relatively moving the ophthalmic means relative to the patient's eye;

a photographing optical system including a plurality of photoelectric photographing elements for photographing the patient's eye;

detecting means which captures image signals of interlaced scanning from the plurality of photoelectric photographing elements at time intervals and detects a position of the patient's eye based on the captured image signals; and control means which controls the moving means based on the results detected by the detecting means to move the ophthalmic means to a desired position relative to the patient's eye.

10. The ophthalmic apparatus according to claim 9, wherein the plurality of photoelectric photographing elements include:

one photoelectric photographing element disposed in a photographing optical path; and another photoelectric photographing element disposed in a divided optical path by a beam splitter disposed in the photographing optical path.

11. The ophthalmic apparatus according to claim 10, wherein the two photoelectric photographing elements are disposed such that each position of pixels of the photoelectric photographing elements coincides with each other relative to a principal optical axis of the photographing optical path in which each of the photoelectric photographing elements is disposed.

12. The ophthalmic apparatus according to claim 9, wherein the detecting means includes means for obtaining a pupil edge of the patient's eye from the obtained image data.

13. The ophthalmic apparatus according to claim 9, wherein the detecting means includes means for obtaining a pupil center position of the patient's eye from the obtained image data.

14. The ophthalmic apparatus according to claim 9, wherein the ophthalmic means includes laser treatment means for treating the patient's eye with a treatment laser beam.

* * * * *